United States Patent
Stephan et al.

(10) Patent No.: US 7,767,942 B2
(45) Date of Patent: Aug. 3, 2010

(54) METHODS FOR MANUFACTURING CERAMIC PARTS USING MICROWAVE SINTERING

(75) Inventors: Marc Stephan, Lorrach (DE); Markus Vollmann, Bad Sackingen (DE); Norbert Thiel, Bad Sackingen (DE)

(73) Assignee: Vita Zahnfabrik H. Rauter GmbH & Co. KG (DE)

( * ) Notice: Subject to any disclaimer, the term of this patent is extended or adjusted under 35 U.S.C. 154(b) by 771 days.

(21) Appl. No.: 10/520,722

(22) PCT Filed: Jul. 5, 2003

(86) PCT No.: PCT/EP03/07212

§ 371 (c)(1),
(2), (4) Date: Dec. 1, 2005

(87) PCT Pub. No.: WO2004/009513

PCT Pub. Date: Jan. 29, 2004

(65) Prior Publication Data

US 2006/0191916 A1    Aug. 31, 2006

(30) Foreign Application Priority Data

Jul. 19, 2002 (DE) ............................. 102 32 818
Nov. 20, 2002 (EP) ............................. 02025674

(51) Int. Cl.
*H05B 6/64* (2006.01)

(52) U.S. Cl. .................. 219/686; 219/679; 219/759; 219/745

(58) Field of Classification Search ............. 219/678, 219/679, 759; 419/48–53; 433/215, 228.1; 264/432

See application file for complete search history.

(56) References Cited

U.S. PATENT DOCUMENTS

| | | | | |
|---|---|---|---|---|
| 4,810,846 A * | 3/1989 | Holcombe et al. | ........... | 219/762 |
| 4,938,673 A | 7/1990 | Adrian | ........... | 419/23 |
| 5,057,659 A | 10/1991 | Schneider et al. | ........... | 219/730 |
| 5,194,408 A | 3/1993 | Stamp et al. | | |
| 5,874,377 A * | 2/1999 | Apte et al. | ........... | 501/97.2 |
| 6,325,839 B1* | 12/2001 | Prasad et al. | ........... | 75/247 |
| 2002/0106611 A1* | 8/2002 | Bhaduri et al. | ........... | 433/201.1 |

FOREIGN PATENT DOCUMENTS

| | | | |
|---|---|---|---|
| JP | 11-157939 | * | 6/1999 |
| WO | WO 94/19917 | | 9/1994 |

OTHER PUBLICATIONS

International Preliminary Examination Report dated Oct. 29, 2004.
International Search Report dated Sep. 15, 2003 for the corresponding PCT Application Serial No. PCT/EP03/07212.

* cited by examiner

*Primary Examiner*—Quang T Van
(74) *Attorney, Agent, or Firm*—Ohlandt, Greeley, Ruggiero & Perle, LLP

(57) ABSTRACT

A method for manufacturing ceramic parts with a certain porosity by sintering using microwaves, the materials to be sintered being arranged in a vessel, wherein the microwaves introduce sintering energy into the materials to be sintered via electromagnetic waves in the range of vacuum wavelengths between 5 cm-20 cm in multimode having an electromagnetic power of up to one kilowatt, and besides being built from primary materials for the structure of the vessel, the vessel is built from a secondary material which comprises, in particular, a mixture of or mixed crystals of non-metallic, para-, ferro- or antiferromagnetic materials.

10 Claims, 4 Drawing Sheets

METHODS FOR MANUFACTURING CERAMIC PARTS USING MICROWAVE SINTERING

FIELD OF THE INVENTION

The preset invention refers to the thermal densification of porous ceramic parts, in particular with a small material volume of up to 10 cm³. The thermal densification is effected by electromagnetic radiation in the wavelength range of 5 to 20 cm using dissipative electric or magnetic polarization effects of the material. Further, the invention refers to a vessel or a device for performing the method.

DISCUSSION OF THE BACKGROUND ART

Presently, such methods are used in drying, removing binding agents and sintering very large ceramic components in an industrial production scale. The advantages of this method lie with the clearly lower energy consumption, the more homogeneous heating (lower temperature gradient) and reduced densification times. This results in an economic production process.

These methods are still critical for oxide ceramics such as $Al_2O_3$ and $ZrO_2$ in that no effective electromagnetic dissipation occurs at ambient temperature. Until today, this obstacle was obviated using a conventional heating, since the effectiveness of the dissipative coupling of the super high frequency waves increases drastically from a certain temperature. However, this increases the time and energy input so that the above mentioned advantages of this technology are greatly relativized. Avoiding the conventional heating can be achieved by adding suitable materials that show significant polarization losses already at ambient temperature, or by suitable sintering additives. This method has disadvantages in the reduced mechanical properties of the cooling ceramics as compared to the pure material. They are especially unsuitable for use in prosthetic medical products for aesthetic and biocompatibility reasons.

Moreover, the question of insulating material for thermal insulation of the baking chamber from the environment is still unanswered for large scale industry purposes. The difficulty lies with the low thermal conductivity and the simultaneous high transparency to super high frequency waves The technical problem the invention is based on was to provide a method, and a vessel for performing this method, which would allow to use microwave treatment also other fields than in large scale industry, especially in the field of dental ceramics.

SUMMARY OF THE INVENTION

The technical problem is solved with a method for manufacturing ceramic parts with a certain porosity by sintering using microwaves, the materials to be sintered being arranged in a vessel, wherein the microwaves introduce sintering energy into the materials to be sintered via electromagnetic waves in the range of vacuum wavelengths between 5 cm-20 cm in multimode having an electromagnetic power of up to one kilowatt, and besides being built from primary materials for the structure of the vessel, the vessel is built from a secondary material which comprises nonmetallic, para-, ferro- or antiferromagnetic materials.

The present invention solves the above mentioned problems by using non-metallic para-, ferro- or antiferromagnetic materials that are suitable as a crucible material that is characterized by dissipative partial absorption of the electromagnetic super high frequency waves at ambient temperature, a high melting point and a partial transparency to super high frequency waves even at high temperatures (up to 1,800° C., in particular up to about 2,000° C.).

Using this so-called secondary material in a vessel has the advantage of a contamination-free densification of the primary material the vessel is otherwise made of. The primary material is supported in the vessel, such as a crucible, for example by high temperature resistant anorganic fiber materials with low absorption of super high frequency waves and low thermal conductivity. These are known per se in the field of the construction of high temperature kilns. The fact that this fiber material only serves as a support, the above mentioned disadvantages are eliminated. Preferred vessel materials are, above all, non-metallic para-, ferro- or antiferromagnetic materials, such as the oxides of chromium, iron, nickel and manganese and the Spinell or Perowskit structures to be derived therefrom (formed with metalloxide without significant absorption of super high frequency waves, e.g. ZnO) or ferro- or antiferromagnetic Spinell materials, such as zincochromite, or ferroelectric Perowskit materials such as barium strontium titanates. It is advantageous that the melting temperature of these materials be as high as possible. If this is not the case, a refractory non-metallic material with a high transparency to super high frequency waves, such as zinc oxide, should be admixed. The advantage of this design of the super high frequency wave kiln is that even at powers of 1 kilowatt at 2.45 GHz in multi-mode, a high temperature of 1,800° C. is achieved. Thus, this kiln becomes very low-priced and smaller than conventional kilns for this temperature range.

In the present method, the material used advantageously is a para-, ferro- or antiferromagnetic material such as zincochromite or a ferroelectric material such as barium strontium titanate.

The advantages of certain antiferromagnetic Spinell structures lie with the high melting temperature and the power dissipation of microwave radiation at the typical frequency in the range from 2-3 GHz, preferably 2.3-2.6 GHz, and most preferred 2.45 GHz, the dissipation being high already at ambient temperature.

In one embodiment of the present method, the wavelength range of the electromagnetic waves is from 11 to 13 cm.

This is the frequency range most common in consumer electronics so that significant cost savings are realized.

The ceramic parts obtained according to the invention have a porosity of 0-50 percent by volume, preferably 10-30 percent by volume. The porosity can be controlled through the sintering temperature. Densely sintered ceramic materials (porosity of nearly 0%) have the advantage of high strength in combination with a high translucence.

According to the invention, a glass could be infiltrated into the ceramic parts to obtain the final strength of the products manufactured.

The porous parts can later be finished easily and be solidified by suitable infiltration methods on the basis of anorganic glasses (e.g. lanthanum silicate glasses) or organic materials (e.g. UDMA, bis-GMA).

The present method allows for a sintering of the ceramic parts to a defined final density. Until today, achieving high final densities for ceramic materials, such as aluminium oxides or zirconium oxides, has been possible only with very high time input and expensive conventional heating methods.

The present method is particularly useful in the manufacture of dental restorations.

To comply with aesthetic requirements, dental ceramic frame parts could be veneered with suitable glass materials, such as feldspar glass, lithium disilicate glass or fluoroapatite glass.

In one embodiment of the present invention, the materials used to manufacture dental ceramic restorations consist of $Al_2O_3$, Spinell, Ce- or Y-stabilized $ZrO_2$ (e.g. TZP, PSZ) or mixtures of these materials.

These ceramic materials show the highest values of strength and fracture toughness of ceramic materials.

According to the invention, full ceramic dental restorations can be made from dental ceramic masses, such as feldspar glass, lithium disilicate glass or fluoroapatite glass, the present method being adapted for use as pressing oven or a preheating oven in glazing full ceramic dental parts or, e.g., for pressed ceramics for dental purposes.

In this case, the advantages are the clearly reduced process time and simultaneously reduced energy input and, thus, costs.

To increase the dense sintering temperature, the invention provides that the material of the vessel may be a mixture of that material with a refractory non-metallic material with a high transparency to super high frequency waves in a wide temperature range.

If the secondary material is only one substance that has a high microwave absorption at ambient temperature, the microwave amplitude can be decreased to an extent that the material to be sintered will no longer be heated sufficiently.

In particular, the refractory non-metallic material with high transparency to super high frequency waves is zinc oxide.

Zinc oxide has a high melting temperature of about 2,000° C.

The invention further refers to a vessel that is particularly suitable for carrying out the above method. According to the invention, the vessel has a primary and a secondary material, the secondary material including a non-metallic para-, ferromagnetic or antiferromagnetic material. Because such a secondary material is provided in the vessel, it is possible to achieve a high temperature in the vessel at ambient temperature and within short time, in particular within a few seconds. Temperatures of about 2,000° C. can be achieved. Thus, it is also possible to sinter oxide ceramics without providing a conventional auxiliary heating. This is possible with conventional microwave means operating in a range of about 700 Watt and being operated according to the multi-mode method.

It is particularly preferred to make the vessel from materials that have been described above in the context of the method. Preferably, the secondary material is a mixture of para-, ferro- or antiferromagnetic materials, such as zincochromite ($ZnCr_2O_4$) with 0-99 percent by weight of zincite (ZnO).

Preferably, the present vessel has a receiving portion into which the material to be sintered is placed. In this particularly preferred embodiment, the receiving portion is at least partly surrounded by secondary material. For example, the receiving portion is cylindrical and is surrounded by a circular ring of secondary material. Preferably, a plurality of secondary material elements are provided surrounding the receiving portion. Thus, a plurality of elements is provided that do not form a closed ring or the like. For example, the secondary material elements are a plurality of ring segments. However, the secondary material elements ma have any other shape, such as a rod shape, or they may have a polygonal, in particular a rectangular cross-sectional shape.

It is preferably preferred to have the secondary material be surrounded by the primary material. Hereby, the secondary material serving to generate the temperature is arranged close to the receiving portion, yet a direct contact between the secondary material and the material to be sintered is avoided.

BRIEF DESCRIPTION OF THE DRAWINGS

The following is a detailed description of the invention using preferred embodiments and making reference to the accompanying drawings. In the figures.

DETAILED DESCRIPTION OF THE PREFERRED EMBODIMENT

Figure 1:
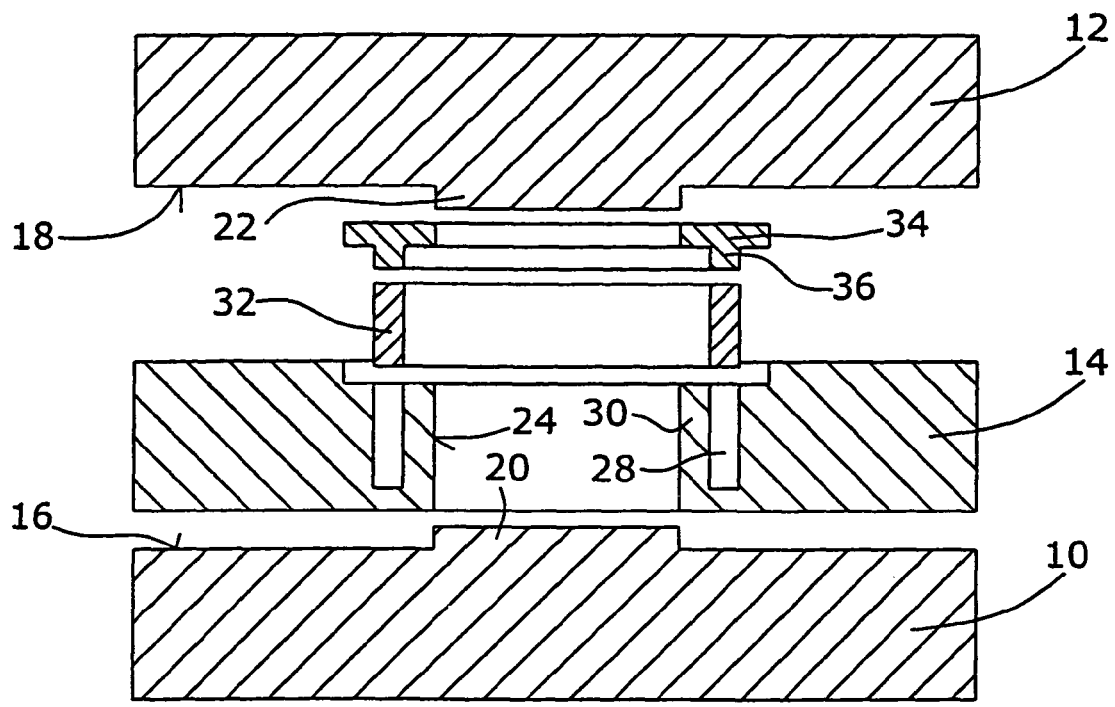
FIG. 1 illustrates a schematic exploded sectional view of a first preferred embodiment of the vessel according to the present invention.

The first embodiment (FIGS. 1-3) of the present vessel for carrying out the present method for manufacturing ceramic parts comprises a bottom element 10, a cover element 12 and an intermediate element 14. The elements 10, 12, 14 are preferably made from primary material. The bottom element 10 and the cover element 12 are cylindrical in shape and each have a cylindrical projection 20 or 22 located on the inner surface 16 or 18, respectively. The intermediate element 14 is annular in shape and has a cylindrical opening 24 which, in the assembled condition (FIG. 2), defines the receiving portion 26. The diameter of the cylindrical opening 24 corresponds to the diameters of the cylindrical projections 20 and 22. In the assembled condition, this results in a cylindrical closed receiving portion 26.

The intermediate element 14 has an annular recess 28 for receiving secondary material. The recess 28 surrounds the receiving portion 26, where the recess does not necessarily have to be a circular ring. In the preferred embodiment illustrated in FIGS. 1 to 3, the recess 28 is of circular ring shape and completely surrounds the receiving portion 26. A wall 30 is formed between the receiving portion 26 and the circularly annular recess 28, the wall being made from primary material as is the entire intermediate element 14. Thus, the secondary material is surrounded by primary material. Either a secondary material element 32 of secondary material is placed into the circularly annular recess 28, or the secondary material 32 is filled into the annular shape. The recess 28 is then closed with a closure element 34, preferably also made from primary material. The closure element 34 also is an annular element with an annular projection 36 extending into the recess 28 (FIG. 2).

The secondary material element 32 and, thus, the secondary material, preferably extends over a large part, especially more than two thirds, of the height of the receiving portion 26. It is particularly preferred to have the secondary material extend over the entire height of the receiving portion.

It is further possible, in FIG. 2, to provide elements of secondary material below and/or above the receiving portion 26.

Figure 4:
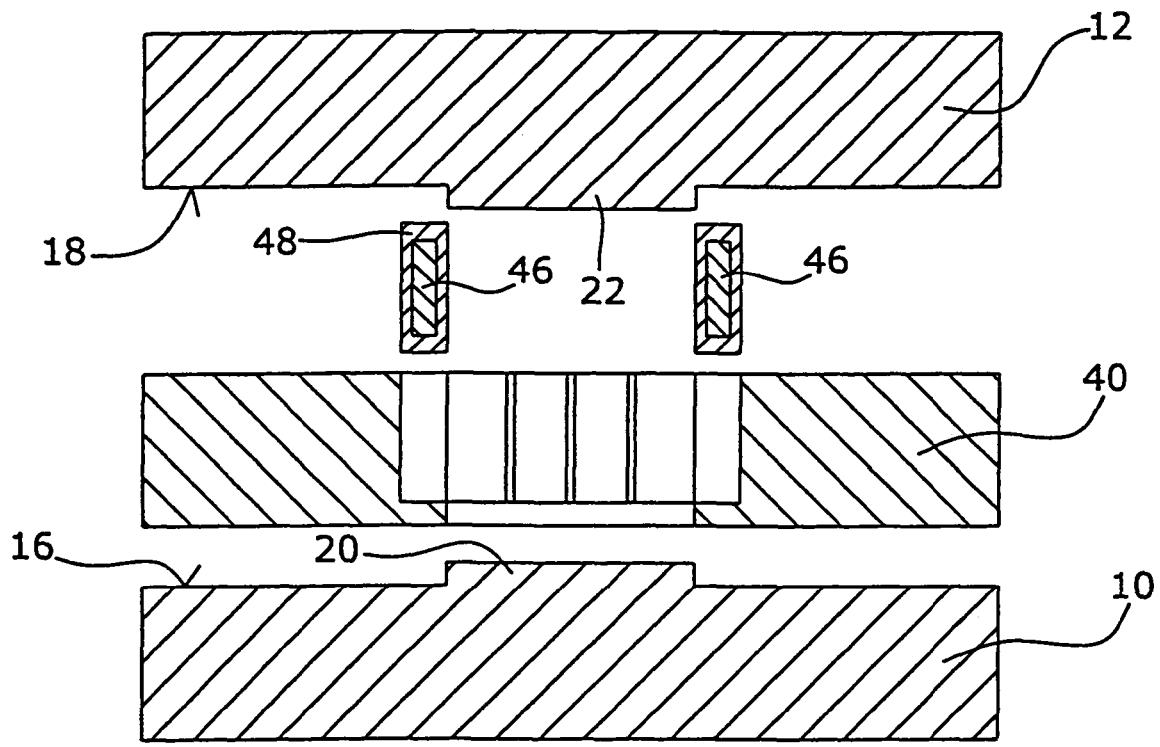
FIG. 4 is a schematic exploded sectional view of a second preferred embodiment of the vessel according to the present invention.
Figure 5:
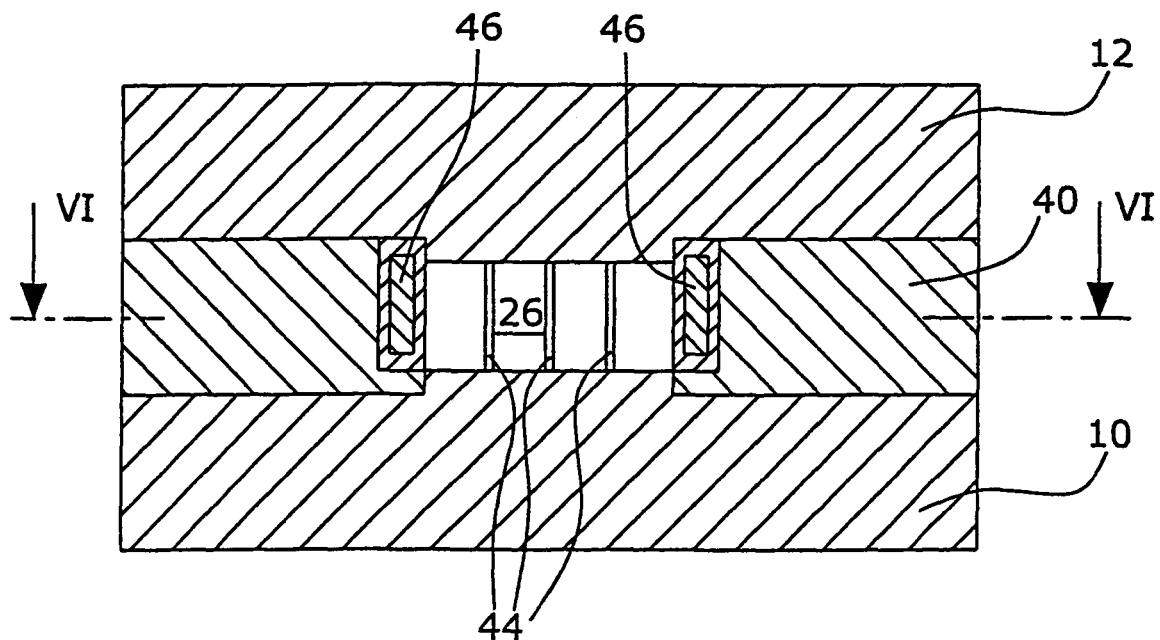
FIG. 5 is a schematic sectional view of the second embodiment of the vessel according to the preferred vessel.
Figure 6:
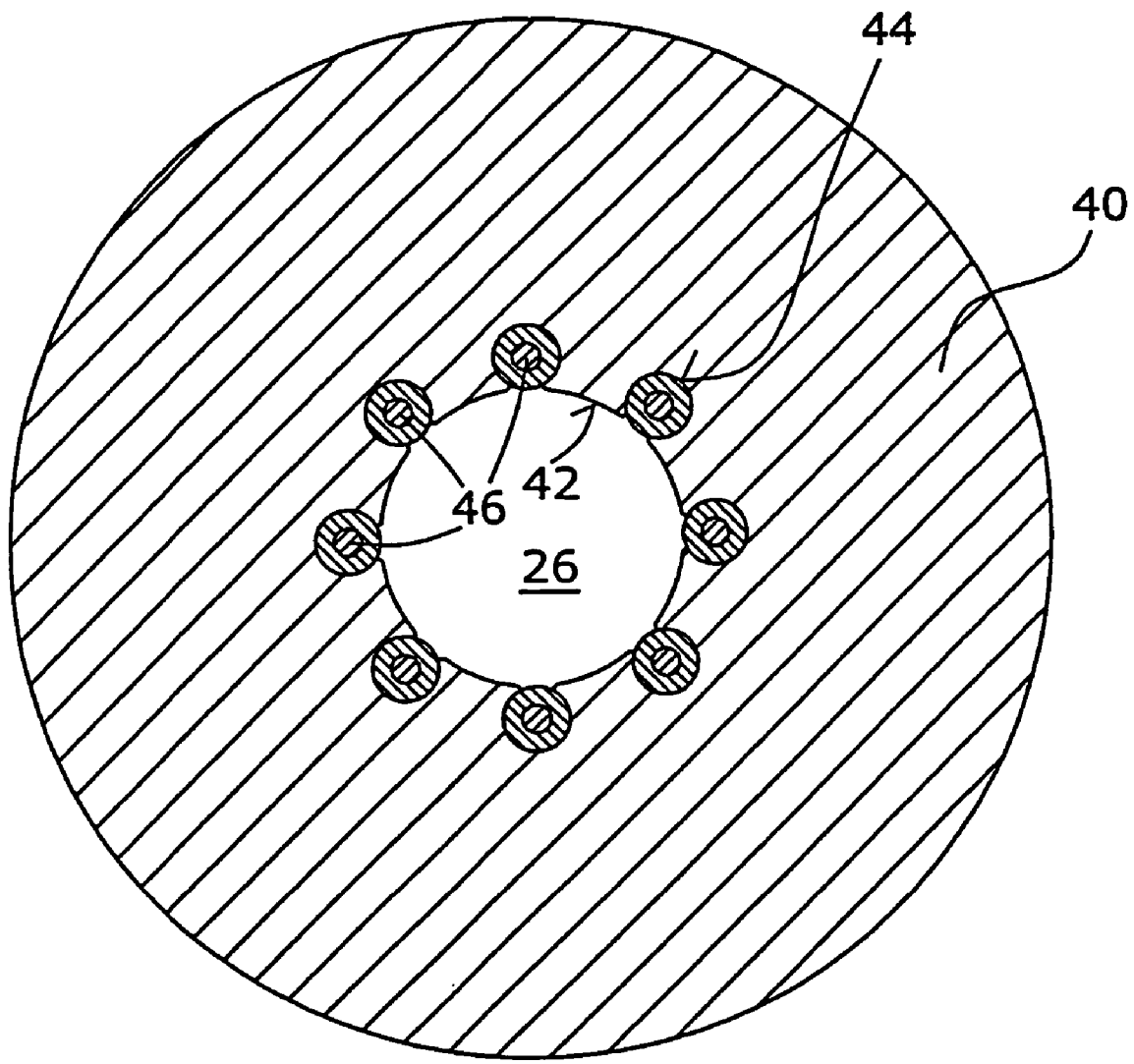
FIG. 6 is a schematic sectional view along line VI-VI in FIG. 5.

In the second preferred embodiment (FIGS. 4-6), elements similar or identical to those in the first embodiments (FIGS. 1-3) bear the same reference numerals.

The bottom element 10, as well as the cover element 12 are substantially identical. An intermediate part 40 also has a circular cross section. A substantially cylindrical receiving portion 26 is formed through the intermediate part 40. However, the inner wall 42 (FIG. 6) of the receiving portion 26 is not smooth. Rather, cylindrical chambers 44 are provided starting from the inner wall 42. Individual rod-shaped secondary material elements 46 are inserted into the cylindrical chambers 44. In the embodiment illustrated, the secondary material elements 46 are encapsulated. The secondary material elements 46 are thus entirely enclosed by a shell layer 48. The shell layer 48 preferably consists of primary material.

Figure 2:
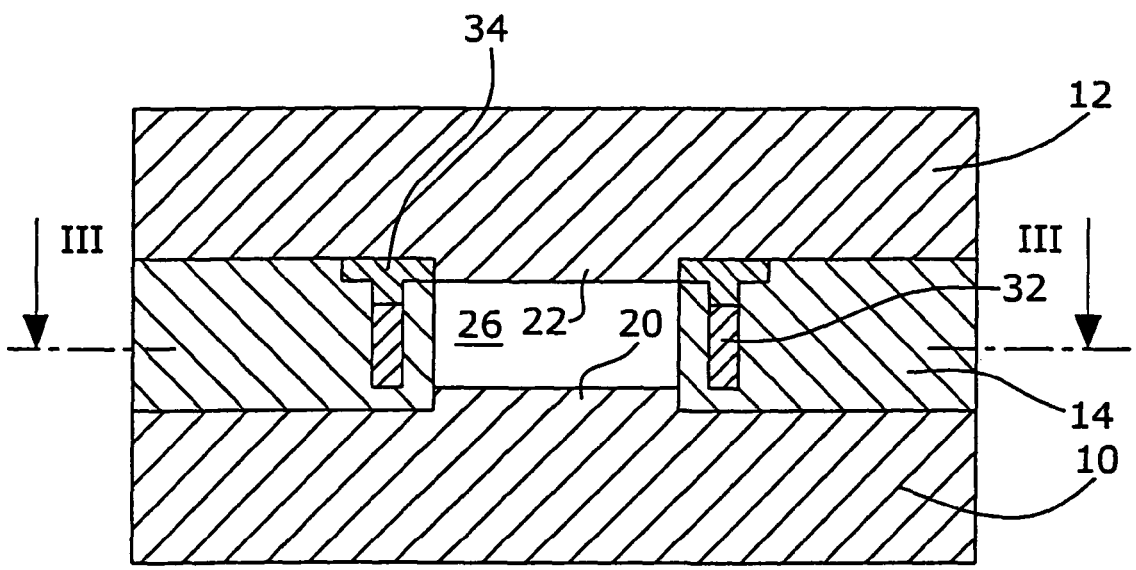
FIG. 2 is a schematic side elevational view of a first preferred embodiment of the vessel.
Figure 3:
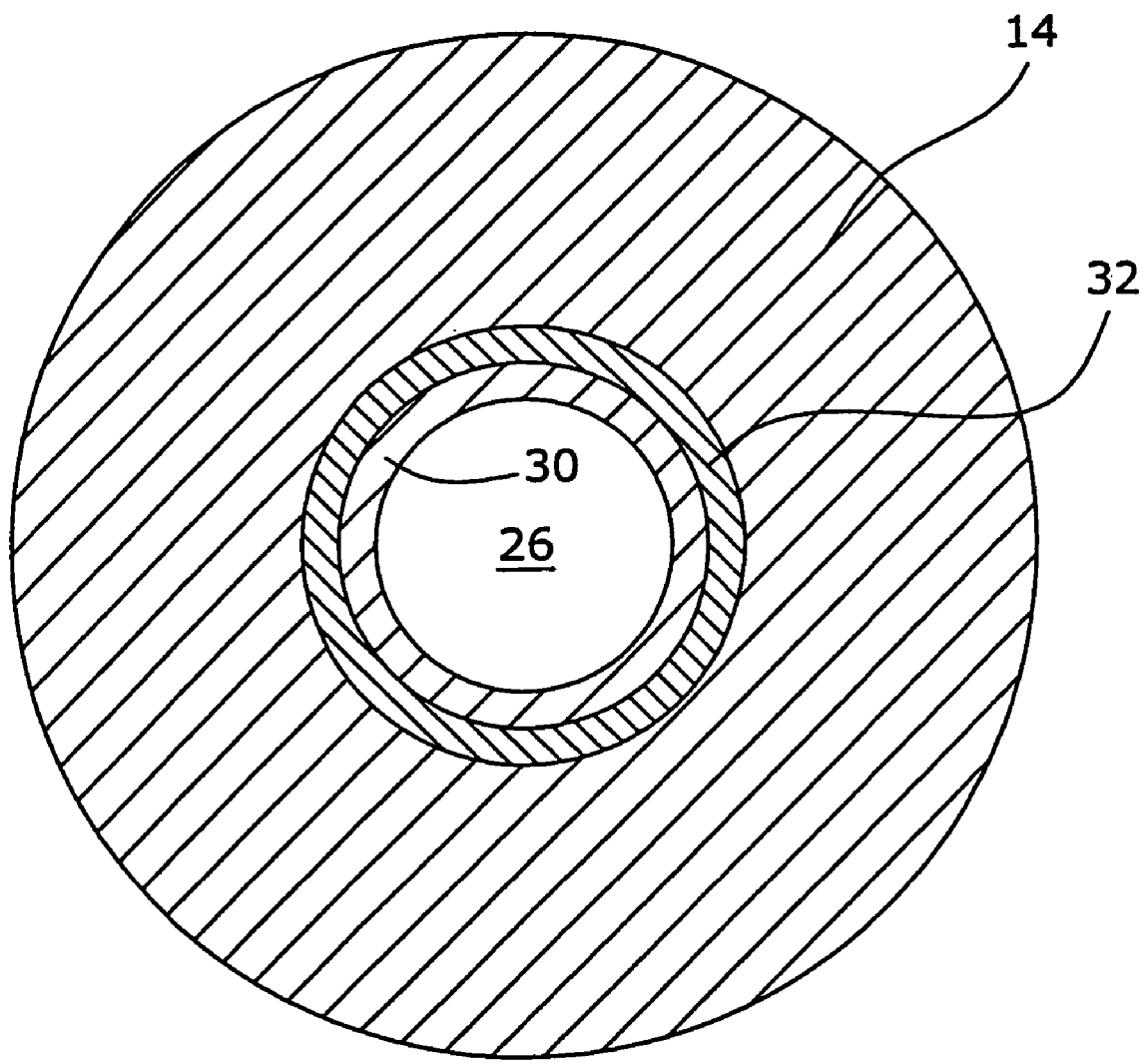
FIG. 3 is a schematic sectional view taken along the line III-III in FIG. 2.

In the following, the present invention will be explained in more detail with reference to two examples:

A vessel of high-temperature resistant aluminium oxide material (resistant to up to 1,800° C.) was made with the vessel shape illustrated in FIGS. 1-3. This was filled with a secondary material 32 in the annular indentation or recess 28. The secondary material was a mixture or comprised mixed crystals of 50 percent by weight of zincochromite ($ZnCr_2O_3$) and 50 percent by weight of zincite ($ZnO$).

EXAMPLE 1

The material to be sintered was a dental crown material of yttrium-stabilized zirconium oxide. This crown cap was placed into receiving portion 26 in the vessel on aluminium oxide baking wool and put into a conventional microwave (900 W, multi-mode, 2.45 GHz) together with the vessel. The same is operated for 15 minutes at a power of 700 W. The final density of the zirconium oxide material is 6.06 g/cm$^3$ and thus corresponds to the theoretical density of the material.

EXAMPLE 2

The material to be sintered is a three-part dental bridge with an overall length of 35 mm prior to dense sintering. This three-part bridge is placed into the vessel on an aluminium oxide baking substrate and put into conventional microwave (see above) together with the vessel. The same is operated for half an hour at a power of 700 W. The final density of the zirconium oxide material is 6.0 g/cm$^3$ and thus corresponds to the theoretical density of the material.

The invention claimed is:

1. Method for manufacturing ceramic parts with a certain porosity by sintering using microwaves, the materials to be sintered being arranged in a vessel, said method comprising:
   assembling a bottom element, an intermediate element, and a top element to define a receiving portion, the bottom, intermediate, and top elements being formed from a primary material;
   introducing a secondary material into an annular recess of the intermediate element so that the secondary material is surrounded by the primary material, the annular recess surrounding the receiving portion, wherein the secondary material comprises at least one material selected from the group consisting of: non-metallic materials, para-magnetic materials, ferro-magnetic materials and antiferromagnetic materials;
   introducing the materials to be sintered into the receiving portion; and
   introducing microwave sintering energy into the materials to be sintered via electromagnetic waves in the range of vacuum wavelengths between 5 cm-20 cm in multimode having an electromagnetic power of up to one kilowatt.

2. Method of claim 1, wherein introducing the secondary material into the annular recess comprises introducing a secondary material element into the annular recess.

3. Method of claim 1, wherein said wavelength range of the electromagnetic waves is between 11-13 cm.

4. Method of claim 1, wherein said ceramic parts have a porosity of between 0-50 percent by volume.

5. Method of claim 4, wherein said porosity is between 10-30% by volume.

6. Method of claim 1, wherein said ceramic parts are infiltrated with a glass material to produce the final strength.

7. Method of claim 1, wherein said ceramic parts are sintered to a defined final density of at least 80% of the theoretical density of the respective material.

8. Method of claim 1, wherein said ceramic parts are dental restorations.

9. Method of claim 8, wherein said dental restorations are veneered using a glass material.

10. Method of claim 1, wherein said material is selected from the group consisting of: $Al_2O_3$, Spinell, Ce- or Y-stabilized $ZrO_2$, and mixtures thereof.

* * * * *